(12) United States Patent
Scheker

(10) Patent No.: US 8,333,806 B2
(45) Date of Patent: *Dec. 18, 2012

(54) WRIST PROSTHESIS

(75) Inventor: Luis Roman Scheker, Glenview, KY (US)

(73) Assignee: Aptis Medical, LLC, Louisville, KY (US)

( * ) Notice: Subject to any disclaimer, the term of this patent is extended or adjusted under 35 U.S.C. 154(b) by 297 days.

This patent is subject to a terminal disclaimer.

(21) Appl. No.: 12/098,034

(22) Filed: Apr. 4, 2008

(65) Prior Publication Data

US 2009/0254189 A1 Oct. 8, 2009

Related U.S. Application Data

(63) Continuation of application No. PCT/US2006/039468, filed on Oct. 10, 2006, and a continuation-in-part of application No. 11/306,311, filed on Dec. 22, 2005, now Pat. No. 8,052,757.

(60) Provisional application No. 60/726,113, filed on Oct. 13, 2005.

(51) Int. Cl.
A61F 2/42 (2006.01)

(52) U.S. Cl. ................ 623/21.13; 623/21.11

(58) Field of Classification Search .... 623/21.11–21.17; A61F 2/42

See application file for complete search history.

(56) References Cited

U.S. PATENT DOCUMENTS

| | | | |
|---|---|---|---|
| 3,875,594 A | 4/1975 | Swanson | |
| 4,106,128 A | 8/1978 | Greenwald et al. | |
| 4,158,893 A | 6/1979 | Swanson | |
| 4,164,793 A | 8/1979 | Swanson | |
| 4,178,640 A | 12/1979 | Buechler et al. | |
| 4,180,871 A | 1/1980 | Hamas | |
| 4,198,713 A | 4/1980 | Swanson | |
| 4,229,841 A | 10/1980 | Youm et al. | |
| 4,349,922 A | 9/1982 | Agee | |
| 4,784,661 A | 11/1988 | Beckenbaugh et al. | |
| 5,108,444 A | 4/1992 | Branemark | |
| 5,133,762 A | 7/1992 | Branemark | |
| 5,314,485 A | 5/1994 | Judet | |
| 5,326,364 A | 7/1994 | Clift, Jr. et al. | |
| 5,458,646 A | 10/1995 | Giachino et al. | |
| 5,507,821 A | 4/1996 | Sennwald et al. | |

(Continued)

FOREIGN PATENT DOCUMENTS

DE 10043107 9/2002

(Continued)

OTHER PUBLICATIONS

'Clinical Mechanics of the Hand', Second Edition, 1993 by Mosby—Year Book, Inc., St. Louis, MO.

(Continued)

*Primary Examiner* — David Isabella
*Assistant Examiner* — Marcia Hoffman
(74) *Attorney, Agent, or Firm* — Camoriano & Associates; Theresa Fritz Camoriano; Guillermo Camoriano

(57) ABSTRACT

A wrist replacement prosthesis includes a radial brace member to be secured to the radius bone, an ulna brace member to be secured to the ulna bone, and an articular member to be secured to the carpal bones, the radial brace member and articular member having wide ellipsoidal surfaces, and the ulnar brace member having a ball at one end which is supported by the radial brace member.

11 Claims, 8 Drawing Sheets

U.S. PATENT DOCUMENTS

| | | | |
|---|---|---|---|
| 5,702,470 | A | 12/1997 | Menon |
| 5,782,926 | A | 7/1998 | Lamprecht |
| 5,951,604 | A | 9/1999 | Scheker |
| 6,059,832 | A | 5/2000 | Menon |
| 6,168,630 | B1 * | 1/2001 | Keller et al. .............. 623/21.11 |
| 6,221,073 | B1 | 4/2001 | Weiss et al. |
| 6,284,000 | B1 | 9/2001 | Ege |
| 6,485,520 | B1 | 11/2002 | Hubach et al. |
| 6,712,820 | B2 | 3/2004 | Orbay |
| 8,052,757 | B1 * | 11/2011 | Scheker .................... 623/21.13 |
| 2002/0010511 | A1 | 1/2002 | Michelson |
| 2006/0004462 | A1 * | 1/2006 | Gupta ....................... 623/21.13 |

FOREIGN PATENT DOCUMENTS

| | | |
|---|---|---|
| DE | 10237016 | 2/2004 |
| EP | 34 192 | 8/1981 |
| FR | 2660856 | 10/1991 |
| GB | 2269752 | 8/1993 |
| WO | WO 92/00709 | 1/1992 |
| WO | WO 01/01892 | 1/2001 |

OTHER PUBLICATIONS

Sutter Implants for the Hand and Forearm, brochure by Sutter Corporation; 4 pages; dated Feb. as, 1990.

The Journal of Bone and Joint Surgery, vol. 69-A, No. 7, Sep. 1987, Jayasanker Menon, MD. 'Total Wrist Replacement Using the Modified Volz Prosthesis'.

The Journal of Hand Surgery, vol. 20A No. 1, Hans Christoph Meuli, MD, et al., Jan. 1995, "Uncemented Total Wrist Arthroplasty", pp. 115-121, 802.

'CFV Wrist System', Biomet, Inc., Form No. Y-BMT-152/013190, 1990.

'Silastaic HP 100 Swanson Finger Joint Implant . . . ' Dow Corning Wright Catalog 1988.

'Use of an Ulnar Head Endoprosthesis . . . ' Mayo Clinic College of Medicine, Rochester, MN 55095. Elsevier Inc. 2005.

'Acu-loc Targeted Distal Radius System'. Acumed, Hillsboro, Oregon, c2004.

'The anatomical DVR Surgical Technique', Hand Innovations, from web site Apr. 19, 2005, Miami, Florida.

'Universal 2 Total Wrist Implant System', Kinetikos Medical Incorporated, from web site last modified Oct. 11, 2005. Carlsbad, CA.

'uHead Ulnar Implant System', Small Bone Innovations, from website c2005, Morrisville, PA.

'Total Wrist Implant', Small Bone Innovations, from web site c2005-2006.

'Universal Distal Radius System', Stryker, from web site 2004.

'Evolve Radial Head Plate', Wright, from web site 2004. Arlington, TN.

'Locon VLS Distal Radius System', Wright, from Web site 2004. Arlington, TN.

* cited by examiner

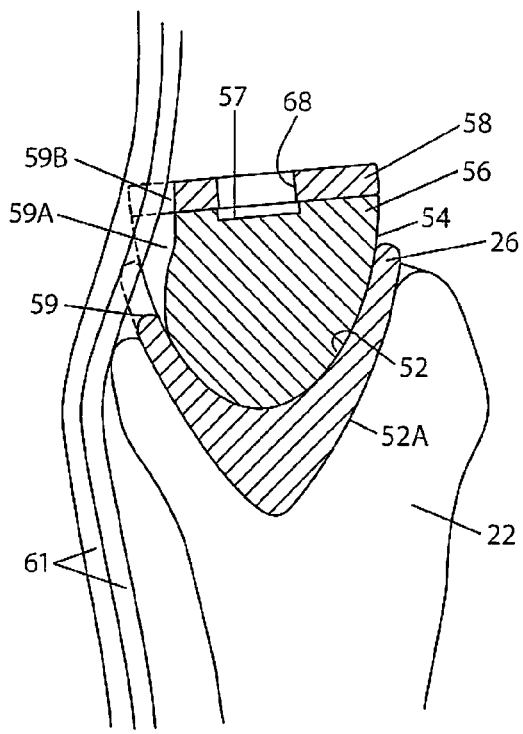
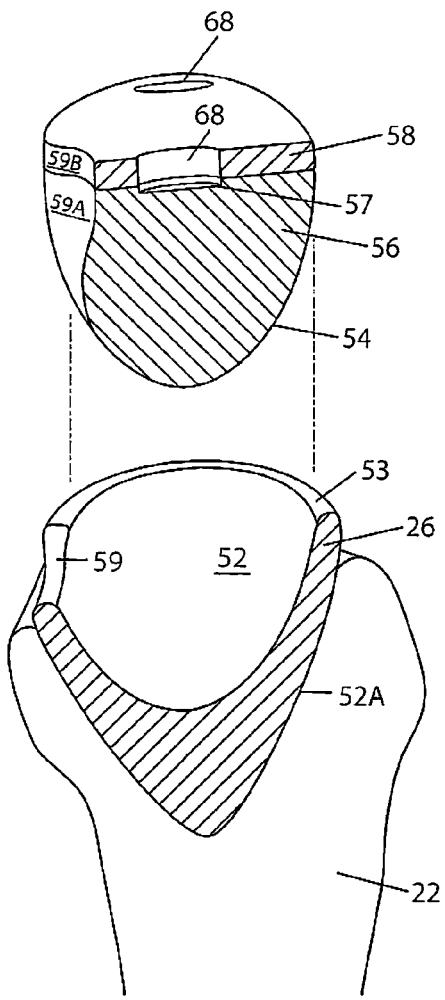
Figure 3E
Figure 3F

WRIST PROSTHESIS

This application is a continuation of PCT/US2006/039468 filed Oct. 10, 2006, which claims priority from U.S. Provisional Application Ser. No, 60/726,113 filed Oct. 13, 2005 and is a continuation-in-part of U.S. patent application Ser. No. 11/306,311, filed Dec. 22, 2005 now U.S. Pat. No. 8,052,757, which are hereby incorporated by reference.

BACKGROUND

The present invention relates to a wrist prosthesis.

BRIEF DESCRIPTION OF THE DRAWINGS

FIG. 3E is a schematic sectional view of the articular socket and articular member of the wrist prosthesis of FIG. 1;

FIG. 3F is a schematic exploded perspective sectional view of the articular socket and articular member of the wrist prosthesis of FIG. 1;

DESCRIPTION

Figure 1:
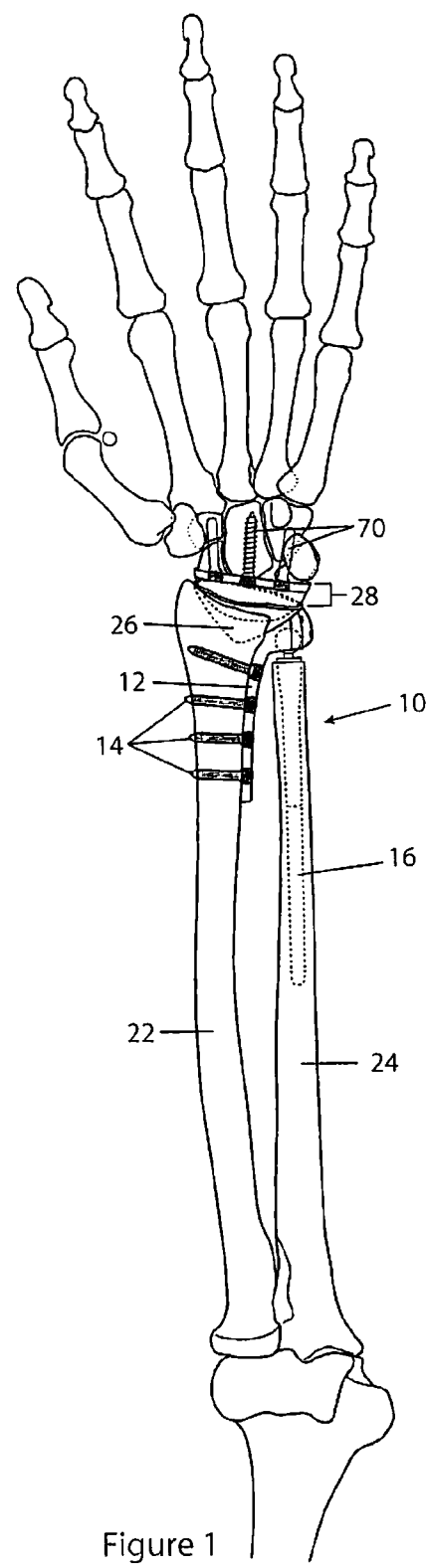
FIG. 1 is a front view of one embodiment of a wrist prosthesis made in accordance with the present invention installed on a human skeleton.

FIGS. 1-3F show one embodiment of a wrist prosthesis 10 made in accordance with the present invention. The wrist prosthesis 10 includes a radial brace member 12, which is secured to the radius bone 22 with a plurality of screws 14. Also included is an ulnar brace member 16, which is secured to the ulna bone 24, typically via a press fit into the medullary cavity 48 of the ulna 24. In addition to (or instead of) the press fit, the brace member 16 may be cemented, adhered, or secured by other means to the ulna 24.

The ulnar brace member 16 is essentially a shaft, symmetrical about a central axis. A spherical ball 18 is mounted onto the shaft 16 at one end. The ball 18 has a bore 50 along its diameter which receives a reduced cross-section end portion 16A of the shaft 16. The ball 18 is free to pivot about the axis of the shaft 16 and to translate axially along the end portion 16A of the shaft 16.

Looking in more detail at the ulnar brace member 16, it includes an elongated ulnar stem rod 46, which is inserted into the medullary cavity 48 (See FIG. 2) of the ulna 24. The ulnar stem rod 46 may be press fit or may be cemented into this medullary cavity 48. In this embodiment, a portion of the ulnar stem rod 46 is coated to provide a porous surface, into which the bone will grow to help secure the rod 46 in position. The reduced diameter distal end 16A of the ulnar stem rod 46 is received in a bore 50 through the diameter of the ball 18 so as to permit translational movement of the ulnar stem rod 46 relative to the ball 18 along the axis of the ulnar brace member 16.

Figure 3:
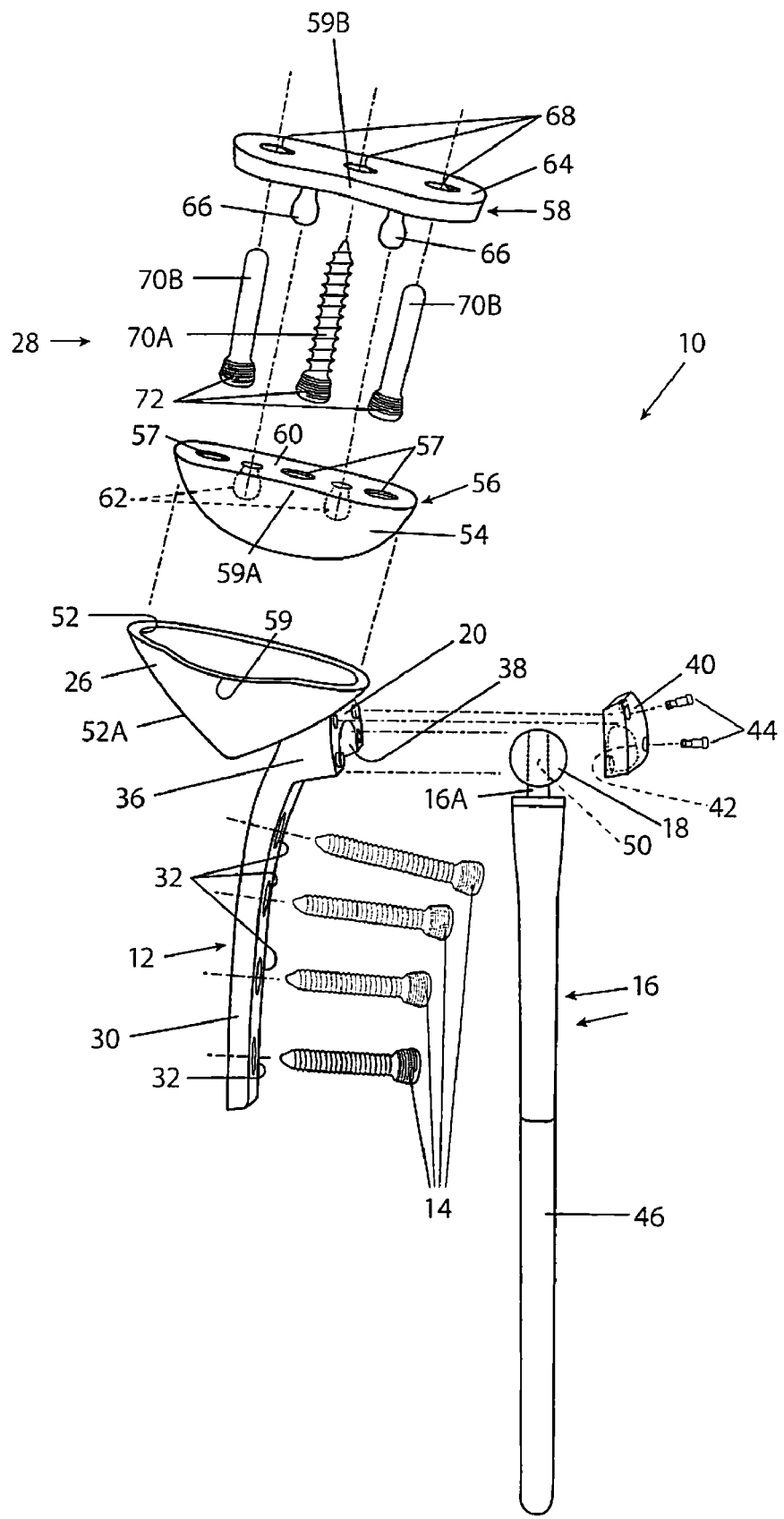
FIG. 3 is an exploded perspective view of the wrist prosthesis of FIG. 1.

As shown best in FIG. 3, the radial brace member 12 includes a base portion 20, which defines a partial spherical cavity 38. The cover 40 also defines a partial spherical cavity 42. When the cover 40 is secured to the base 20 by means of screws 44, the spherical ball 18 of the ulnar brace member 16 is trapped in the partial spherical cavity formed by the base portion 20 and cover 40 and is free to swivel within and bear against the surface of that cavity, in order to support the radius 22 relative to the ulna 24 for pronation and supination of the forearm and for the bearing of weight. The bearing surface 38 is nearly in the position of the sigmoid notch of the original radius, and the ball 18 is nearly in the position of the ulna head of the original ulna, so the joint provides the same relative positions of the radius and ulna throughout the entire pronation and supination of the forearm as would have been provided by the original intact joint. This means both that the axes of the radius 22 and ulna 24 are in the same relative positions and that the longitudinal position of the joint along the axes of both bones is in the same relative position as it would have been in the original joint.

In this particular embodiment, the bearing surface 38 is 1-2 millimeters in the ulnar direction from the original bearing surface that was provided by the cartilage in the sigmoid notch of the original joint, and the ball 18 has a radius that is 1-2 millimeters smaller than the original ulna head, so, while the actual bearing surface is offset 1-2 millimeters in the ulnar direction from the bearing surface of the original intact joint, the relative positions of the bones are the same as in the original intact joint. Obviously, there will be some tolerances involved in the actual production and installation, but it is preferred that the relative positions of the bones be within two millimeters of their original intact positions.

Figure 2:
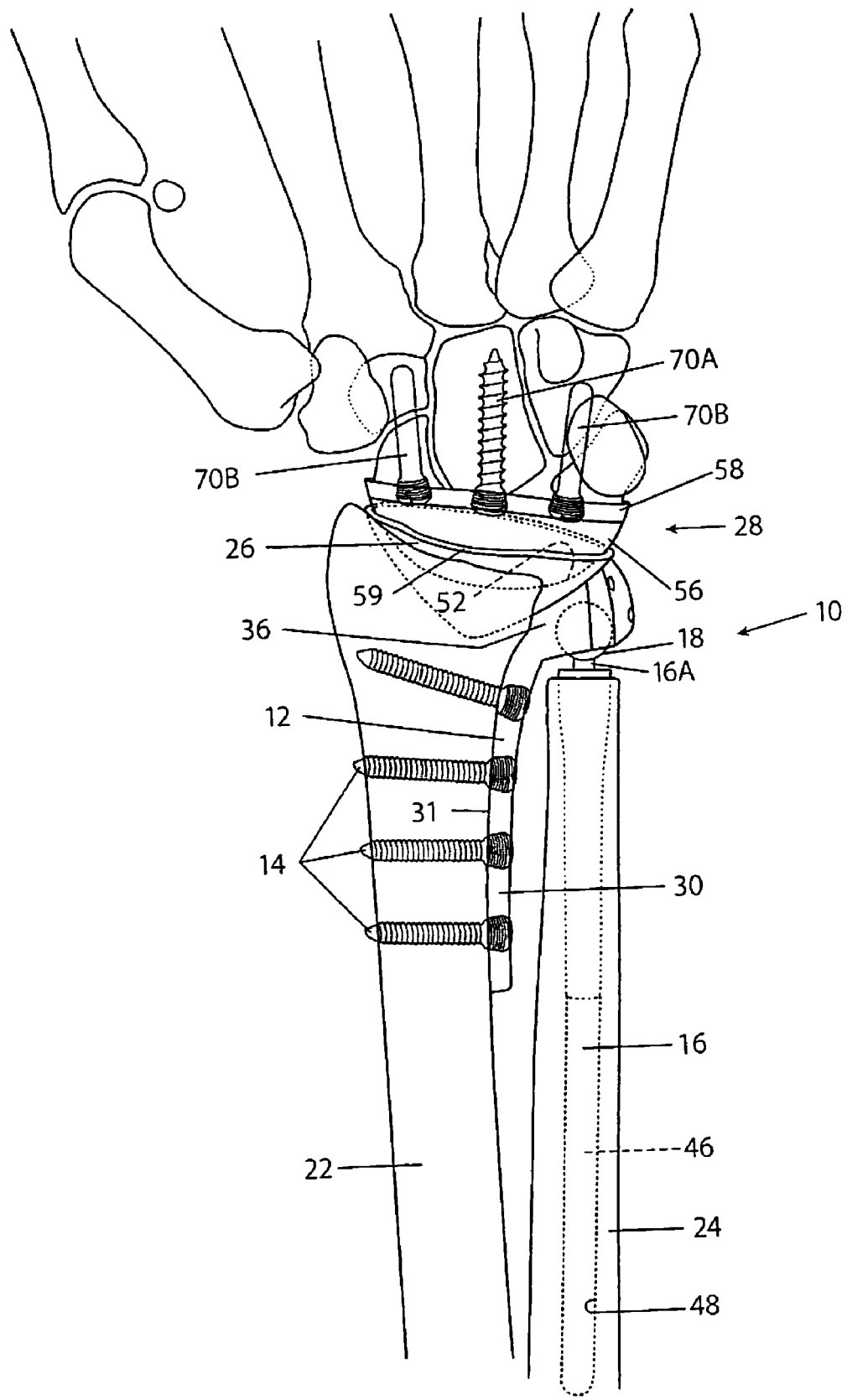
FIG. 2 is an enlarged view of the installed wrist prosthesis of FIG. 1.

Referring to FIGS. 2 and 3, the radial brace member 12 includes an elongated portion 30, which lies adjacent to the outer surface of the radius bone 22 and is secured to the radius 22 by means of screws 14 that extend through threaded openings 32 in the elongated portion 30. A radius abutment surface 31 of the elongated portion 30 conforms to the outer surface of the side of the radius bone 22 that faces the ulna 24, providing a large contact surface between the brace member 12 and the radius bone 22. The particular screws 14 shown here have two different sets of threads. The thread along the shank is threaded into the bone, and the thread along the head is threaded into the respective threaded opening 32. Of course, other types of fasteners could be used instead of or in addition to these screws 14.

As indicated above, the ball 18 also is able to rotate within the partial spherical cavity formed by the base 20 and the base cover 40. This arrangement provides Support of the radius 22 relative to the ulna 24 through the full range of motion from pronation to supination of the hand. The cover 40 ensures that the ball 18 of the ulnar brace 16 will remain engaged with the radial brace 12 so it can bear against the bearing surface 38 to provide the desired support. The cover 40 essentially replaces the function of the ligaments that originally held the radius in position relative to the ulna head. The portion of the prosthesis 10 described thus far is very similar to a distal radioulnar joint replacement prosthesis described in U.S. Pat. No. 5,951,604 "Scheker", which is hereby incorporated herein by reference.

The wrist prosthesis 10 further includes a concave articular socket 26, which is fixed relative to the radial brace member 12, and a convex articular member 28, which is fixed relative to the patient's hand and which fits into and slides relative to the articular socket 26.

In this embodiment, the articular socket 26 is an integral part of the radial brace member 12. Alternatively, the articular socket 26 could be a separate piece which is fixed to the radial brace member 12 by such means as welding, bolting, snapping together, or any other suitable means.

The articular socket 26 defines a concave ellipsoidal surface 52 (which may also be referred to as a reverse-ellipsoidal surface), which receives the mating convex ellipsoidal surface 54 of the articular member 28 as described in more detail below. Since the articular socket 26 is fixed relative to the radial brace member 12, it is supported by and secured to the radius 22 as well as being supported by the ulna 24 through the ball joint. As best shown in FIG. 2, the concave ellipsoidal Surface 52 extends laterally in the direction of the ulna 24 to a point beyond the center of the cavity formed by the partial spherical cavities 38, 42 of the base 20 and base plate 40, which means that it extends beyond the axis of the ulna 24 (and beyond the axis of the ulnar brace 16, with is coaxial with the ulna 24). It also extends in the ulnar direction beyond the bearing surface of the cavity 38, which is in the position of the original sigmoid notch. This allows the articular socket 26 to provide a wider bearing surface than is present in the natural human wrist.

In this embodiment, the articular socket 26 forms a cup with a generally uniform wall thickness, so it also defines a convex outer surface 52A opposite the concave ellipsoidal surface 52 (see FIG. 3). The outer surface 52A of the articular socket 26 generally conforms to the natural recess at the distal end of the radius bone 22, thereby minimizing the amount of the bone that is removed to accommodate the articular socket 26. Usually, only a small amount of bone matter is removed toward the center of the radius bone 22 to receive the articular socket 26, thereby leaving the length of the radius bone unchanged. This is different from the mounting arrangements of the prior art, in which the end of the radius bone 22 typically is cut off flat, thus reducing the length of the bone. There typically is damage to the bone that gives rise to the need for an artificial joint, so the preparation required to mount the radial brace 12 on the radius 22 will vary in each case. However, in a typical case, a small amount of bone matter is removed toward the center of the radius 22 at its distal end to receive the articular socket 26, and any cartilage (if present) is removed from the ulnar side of the radius 22 at the sigmoid notch, so the radial brace 12 can fit snugly against the radius 22. This leaves the radius 22 at its full length. Thus. the shape of the outer surface 52A. which generally conforms to the shape of the natural recess at the distal end of the radius boric 22. and its position relative to the other parts of the prosthesis, provide a means for being received in the natural recess at the distal end of the radius bone without changing the overall length of the radius bone.

In this embodiment, the articular member 28 includes an articular base member 56 and a distal plate 58.

The articular base member 56 defines the convex ellipsoidal surface 54, which mates with and slidably engages the concave ellipsoidal surface 52 of the articular socket 26 for movement of the base 56 relative to the articular socket 26. The top surface 60 of the articular base member 56 is substantially flat and defines three round indentations 57. The flat top surface 60 also defines two tear-shaped cavities 62 for the attachment of the distal plate 58 to the articular base member 56, as described below.

The distal plate 58 is a substantially flat member 64, with two downwardly-extending tear-shaped projections 66. These projections 66 are sized to snap-fit into the corresponding tear-shaped cavities 62 in the base 56 in order to secure the distal plate 58 to the base 56. The distal plate 58 further defines three threaded through openings 68 to accommodate elongated fasteners 70A, 70B, which secure the distal plate 58 to the carpal bones of the hand. (The fasteners could extend into the metacarpals if desired.) The fasteners in this embodiment are a screw 70A and two pegs 70B, as shown in FIG. 3. Each of these fasteners 70A, 70B includes a threaded portion 72 at the head end, which includes self-locking threads that are threaded and locked into the corresponding threaded surface in the respective opening 68 of the distal plate 58. The articular base member 56 includes three round indentations 57 for receiving the heads of the fasteners 70A, 70B.

In this embodiment, the articular socket 26 of the radial brace member 12, as well as the base 56 and distal plate 58 of the articular member 28, further define curved, recessed surface portions 59, 59A, and 59B, respectively, in the front, or volar, side of the prosthesis 10, to provide a guiding surface for guiding the median nerve and flexor tendons 61 over the wrist. This arrangement can be seen best in FIGS. 3E and 3F. While these recessed surface portions are not required, it is preferred that at least the recessed surface portion 59 of the articular socket 26 be provided to help guide and ease the transition of the median nerve and flexor tendons 61 over the wrist.

To help define the orientation of the various parts of the wrist and the components of the wrist prosthesis 10, it should be noted that there is an ulnar side (laterally in the direction of the ulna bone), a radial side (laterally in the direction of the radius bone), a front or volar side (toward the palm), and a back or dorsal side (toward the back of the hand).

In this embodiment, the ellipsoidal surface 52 of the articular socket 26 is wider in the radial-ulnar direction than the volar-dorsal direction, and the radius of curvature in the radial-ulnar direction is greater than the radius of curvature in the volar-dorsal direction. The recesses 59, 59A, 59B are formed in the front, or volar, side of the prosthesis 10, so they essentially replace the proximal portion of the carpal tunnel of the wrist, providing the guiding surface that receives the median nerve and flexor tendons 61 in the wrist as best shown in FIGS. 3E and 3F, which helps reduce wear on the nerve and tendons.

Figure 3A:
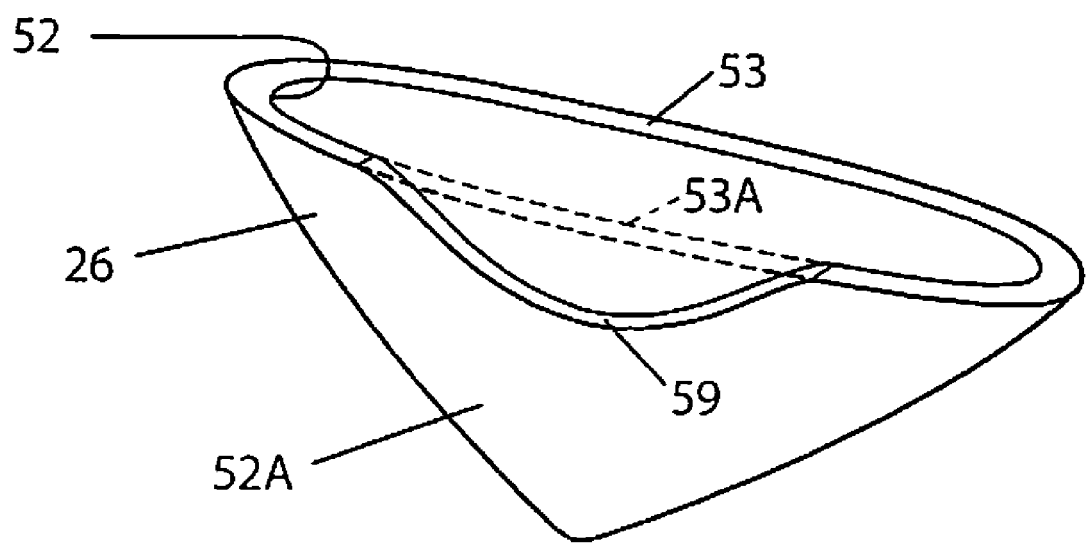
FIG. 3A is a perspective view of the articular socket of the wrist prosthesis of FIG. 1.

FIG. 3A is a detailed view of the articular socket portion 26 of the radial brace member 12, showing that the recess 59 extends from the distal edge 53 of the articular socket 26 towards the proximal end of the articular socket 26 to define a centrally recessed guide surface. The phantom lines 53A in FIG. 3A show what the edge 53 would look like if it were entirely planar, without the central recess 59. As best seen in FIG. 2, the recess 59 is formed on the front, or volar, side of the prosthesis 10 in the location of the carpel tunnel of the natural wrist.

Figure 3D:
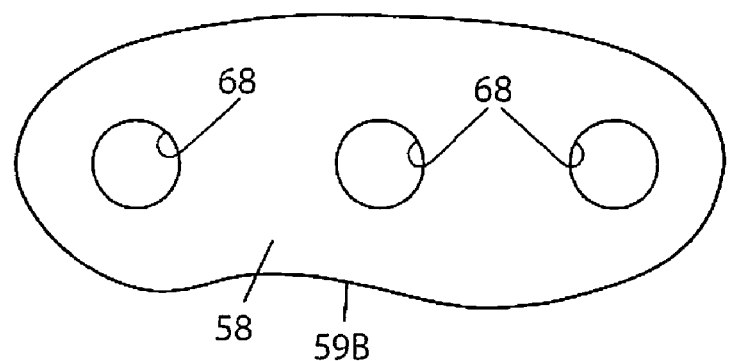
FIG. 3D is a plan view of the distal plate of the wrist prosthesis of FIG. 1.
Figure 3C:
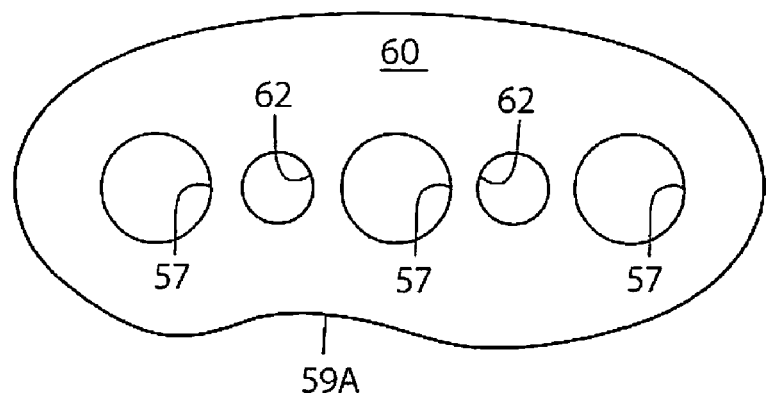
FIG. 3C is a plan view of the articular base member of the wrist prosthesis of FIG. 1.
Figure 3B:
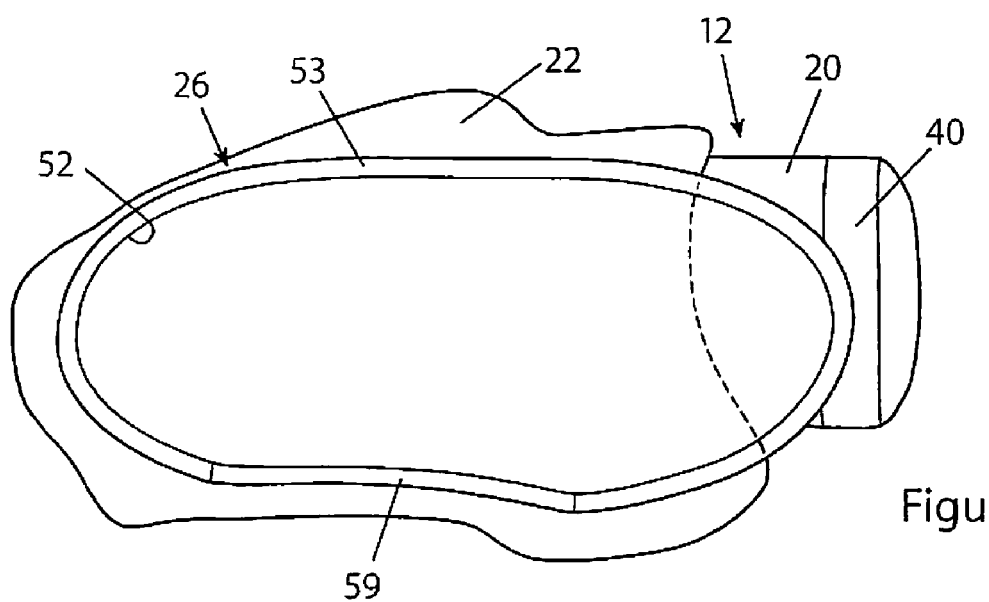
FIG. 3B is a distal end view looking down on the articular socket portion of the wrist prosthesis of FIG. 1.

FIG. 3B is a distal end view of the radial brace member 12 and radius bone 22, looking down on the articular socket 26. In FIGS. 3A and 3B it can be seen that the curved central recess 59 in the articular socket 26 is on the volar side and the distal edge of the curved central recess 59 is concave downwardly, toward the proximal end of the socket 26, and concave inwardly, toward the dorsal side of the socket 26. FIGS. 3C and 3D are distal end views of the articular base member 56 and the distal plate 58, respectively, showing the indentations 57 and tear-shaped cavities 62 in the articular base member 56 and the threaded openings 68 in the distal plate 58. The articular base member 56 has a curved central recess 59A on the volar side, which is concave inwardly, toward the dorsal side, as shown in FIGS. 3C and 3E, and the distal plate 58 also has a curved central recess 59B on the volar side, which is concave inwardly, toward the dorsal side, as shown in FIGS. 3D and 3E. As was explained above, and as shown in FIG. 3E, the curved central recesses 59, 59A, 59B are aligned, and the curved central recess 59A on the articular base member 56 extends proximally to the curved central recess 59 in the articular socket 26 to provide a guide surface that essentially replaces the proximal portion of the carpal tunnel of the natural wrist.

When the articular base member 56 and distal plate 58 are fitted together, with the tear-shaped projections 66 snapped into the tear-shaped recesses 62, to form the articular member 28, the recesses 59A, 59B are aligned with each other. Once the articular member 28 and articular socket 26 are mated together, the recesses 59, 59A, 59B align with each other, providing a guide surface similar to the carpel tunnel of the wrist and guiding the median nerve and flexor tendons. By providing a gradual, guided transition over the wrist, the recesses 59, 59A, 59B reduce wear on the nerve and tendons of the wrist.

FIG. 3B also shows that the ellipsoidal surface 52 of the articular socket 26 is wider in the radial-ulnar direction than the volar-dorsal direction, and it extends across the full width of the wrist in order to provide a large supporting surface area. The ellipsoidal surface 52 extends from a point outside of (or beyond) the longitudinal axis of the radius 22 in the radial direction to a point beyond the axis of the radial brace 12 in the ulnar direction, projecting over a portion of the cover 40, and over both the radial-most and the ulnar-most points on the ball 18 (i.e. the point farthest in the radial direction and the point farthest in the ulnar direction, as shown in FIG. 2). FIG. 3B also shows that the base 20 of the radial brace member 12 is on the ulnar side of the articular socket 26.

In this particular embodiment, the metal components of the prosthesis 10 are made from cobalt chromium. These metal components include the radial and ulnar brace members 12, 16, the cover 40, the securing screws 14, 44, 70A, and pegs 70B, the articular socket 26, and the distal plate 58, including its two tear-shaped projections 66. The non-metal components are made from an ultra-high molecular weight polymer, such as UHMW polyethylene. These non-metal components include the ball 18 and the base 56 of the articular member 28.

To assemble and install the wrist prosthesis 10, first the distal radioulnar joint is installed as described in the aforementioned U.S. Pat. No. 5,951,604 "Scheker", with the only change being that some of the distal end of the radius probably will need to be removed as described earlier in order to receive the articular socket 26. At this point, the radial brace member 12 is secured into the radius 22, the ulnar brace member 16 is secured onto the ulna 24, and the ball 18 is secured in the recess formed between the cover 40 and the base 20 to form a ball joint.

Next, the proximal ends of the carpal bones are excised to fit flat against the distal plate 58 of the articular member 28. With the wrist bent downwardly, holes are drilled in the carpal bones as required (and preferably with the aid of a template) to receive the fasteners 70A, 70B. Then, the fasteners 70A, 70B are extended through the openings 68 in the distal plate 58 and into the holes that have been drilled in the carpal bones, and the fasteners 70A, 70B are rotated to thread them into the threaded openings 68 in the distal plate 58. The head end of the fasteners 70A, 70B has a recess (not shown) that allows a rotational driver such as a screwdriver or Allen wrench to rotationally drive the fasteners. The screw 70A also is threaded into the hole that has been drilled in its respective carpal bone, thereby securing the distal plate 58 to the carpal bones. The screw 70A prevents the distal plate 58 from pulling away from the carpal bones, and the pins 70B prevent the distal plate 58 from rotating or sliding relative to the carpal bones. The pins 70B also prevent the distal plate 58 from pulling away from the carpal bones, because they are inserted at an angle, creating a wedge effect. While one screw 70A and two pegs 70B are shown, any combination of screws and pegs may be used, as well as other fastening means for securing the distal plate 58 to the carpal bones of the wrist. It may be desirable to provide a porous surface on the pegs 70B or other fasteners into which the bone may grow to provide an even more secure attachment.

The wrist is then pushed back up, being careful to align the tear-shaped projections 66 in the distal plate 58 with the tear-shaped cavities 62 in the base 56, and the distal plate 58 and base 56 are pushed together until the tear-shaped projections 66 in the distal plate 58 snap into the tear-shaped cavities 62 in the base 56. The base 56 is then inserted into the cavity 52 of the articular socket 26 to complete the assembly. The existing tendons and ligaments of the wrist help retain the articular member 28 in the articular socket 26 at the distal radius.

This arrangement allows a full range of motion, as well as providing support of the wrist joint by both the radius 22 and the ulna 24. It also should be noted that the distal plate 58 and the corresponding ellipsoidal surfaces of the articular member 28 and the articular socket 26 extend across the full width of the wrist in order to provide a large supporting surface area as the articular member 28 slides within the articular socket 26. The prosthesis is also well-supported by both the radius 22 and the ulna 24, which permits the wrist joint to support a substantial amount of weight or loading without causing pain and without damaging the joint, while permitting a full range of motion that closely mirrors the range of motion of the natural wrist joint.

Figure 4:
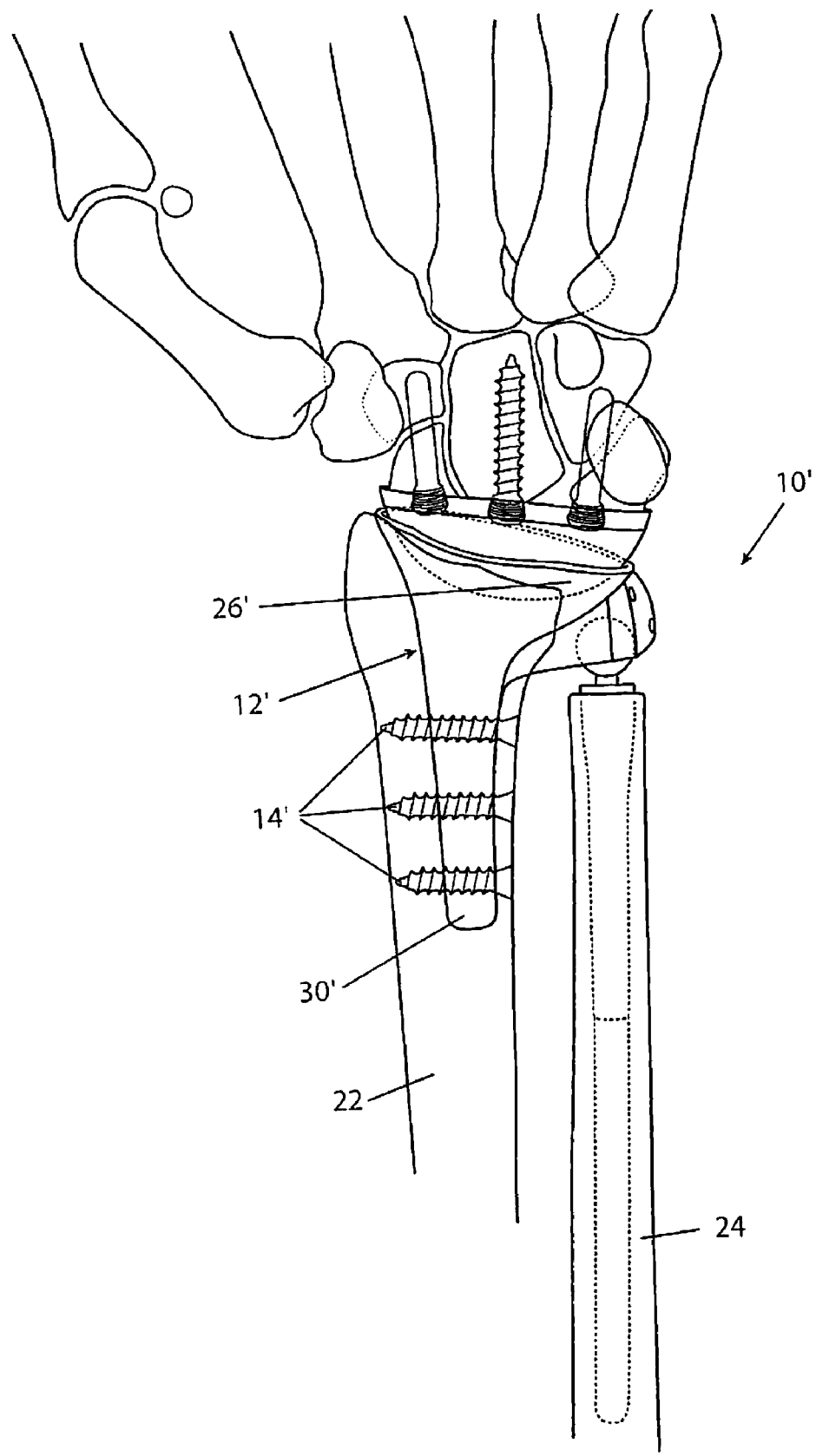
FIG. 4 is a view similar to FIG. 2, but for a second embodiment of an installed wrist prosthesis made in accordance with the present invention.
Figure 5:
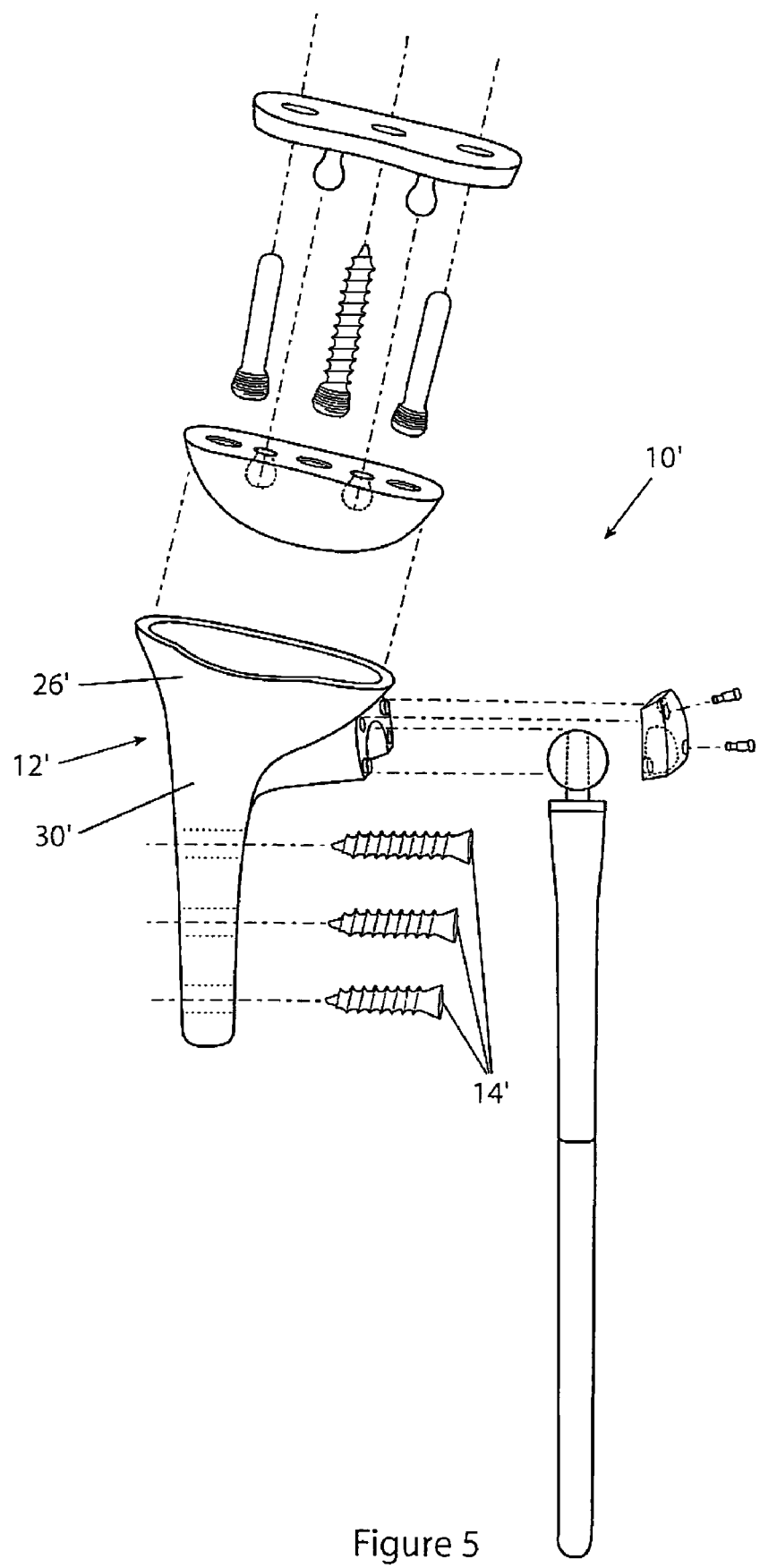
FIG. 5 is an exploded perspective view of the wrist prosthesis of FIG. 4.

FIGS. 4 and 5 show a second embodiment of a total wrist replacement prosthesis 10' made in accordance with the present invention. This embodiment 10' is very similar to the first embodiment 10 described above, except that the location and installation of the radial brace member 12' is different. In this embodiment, the radial brace member 12' is inserted into the medullary cavity of the radius 22, and may make use of cement or other methods of attachment such as screws 14'. All the other components of this embodiment 10' and its method of operation remain substantially the same as in the first embodiment 10. This embodiment provides a larger contact surface area between the articular socket 26' and the elongated portion 30' of the radial brace member 12', which may result in greater structural integrity of the prosthesis 10'. Of course, in this embodiment, more of the central portion of the radius bone 22 would have to be removed in order to mount the radial brace member 12'. However, the full length of the radius bone 22 is still preserved. At this point, the first embodiment of the prosthesis 10 is preferred, as it appears that mounting to the outside of the radius bone 22 provides greater structural support for the prosthesis.

It will be obvious to those skilled in the art that modifications may be made to the embodiments described above without departing from the scope of the present invention as defined by the claims.

What is claimed is:
1. A prosthesis for a wrist joint replacement, comprising:
   a radial brace member having a volar side, dorsal side, radial side, ulnar side, proximal side and distal side, and including a wall at said distal side which defines a first ellipsoidal surface and a distal edge, wherein the volar side of said distal edge defines a centrally recessed guide surface that is concave downwardly, toward in the proximal side, and is concave inwardly, toward the dorsal side; and an articular member defining a second ellipsoidal surface slidably received by said first ellipsoidal surface, one of said first and second ellipsoidal surfaces being convex and the other being concave.

2. A prosthesis for a total wrist and distal radioulnar joint replacement as recited in claim 1, and further comprising:
an ulnar brace member, including
a rod defining a proximal end and a distal end and a longitudinal axis; and
a ball mounted on said distal end for translation along said longitudinal axis relative to said rod; and
wherein said radial brace member further defines a bearing surface which supports said ball for relative movement between the ball and the radial brace member.

3. A prosthesis for a wrist joint replacement, comprising:
a radial brace member having a volar side, dorsal side, radial side, ulnar side, proximal side and distal side, and including a wall at said distal side which defines a first ellipsoidal surface and a distal edge, wherein the volar side of said distal edge defines a centrally recessed guide surface; and
an articular member defining a second ellipsoidal surface slidably received by said first ellipsoidal surface, one of said first and second ellipsoidal surfaces being convex and the other being concave, wherein said articular member defines a volar recessed guide surface aligned with and extending proximally to said centrally recessed guide surface.

4. A prosthesis as recited in claim 3, wherein said volar recessed guide surface is recessed inwardly, towards the dorsal side; and further comprising:
an ulnar brace member including
a rod defining a proximal end and a distal end, and
a ball mounted to said distal end;
wherein said radial brace member defines a bearing surface which receives and supports said ball.

5. A prosthesis for a wrist joint replacement as recited in claim 3, wherein said centrally recessed guide surface of said first ellipsoidal surface is concave inwardly, toward the dorsal side, and the volar recessed guide surface of the articular member is concave inwardly, toward the dorsal side.

6. A prosthesis for a wrist joint replacement, comprising:
a radial brace member having a volar side, dorsal side, radial side, ulnar side, proximal side and distal side, and including a wall at said distal side which defines a first ellipsoidal surface and a distal edge, wherein the volar side of said distal edge defines a centrally recessed guide surface that is concave downwardly, toward the proximal side; and
an articular member defining a second ellipsoidal surface slidably received by said first ellipsoidal surface, one of said first and second ellipsoidal surfaces being convex and the other being concave;
wherein said articular member defines a volar recessed guide surface aligned with and extending proximally to said centrally recessed guide surface.

7. A prosthesis as recited in claim 6, and further comprising:
an ulnar brace member including
a rod defining a proximal end and a distal end, and
a ball mounted to said distal end; and
wherein said radial brace member defines a bearing surface configured for mounting on the radius, which receives and supports said ball for rotation relative to the radius.

8. A prosthesis for a total wrist and distal radioulnar joint replacement, comprising:

a radial brace member having a volar side, dorsal side, radial side, ulnar side, proximal side and distal side, and including a wall at said distal side which defines a first ellipsoidal surface and a distal edge, wherein the volar side of said distal edge defines a centrally recessed guide surface that is concave downwardly, towards the proximal side;
an articular member defining a second ellipsoidal surface slidably received by said first ellipsoidal surface, one of said first and second ellipsoidal surfaces being convex and the other being concave;
wherein said second ellipsoidal surface defines a recess aligned with and extending proximally to the central recess in said first ellipsoidal surface; and
an ulnar brace member, including
a rod defining a proximal end and a distal end and a longitudinal axis; and
a ball mounted on said distal end for translation along said longitudinal axis relative to said rod; and
wherein the radial brace member defines a bearing surface which supports said ball.

9. A prosthesis for a total wrist and distal radioulnar joint replacement, comprising:
an ulnar brace member, including
a rod defining a proximal end and a distal end and a longitudinal axis; and
a ball mounted on said distal end for translation along said longitudinal axis relative to said rod; and
a radial brace member having a volar side, dorsal side, radial side, ulnar side, proximal side and a distal side, and defining a first ellipsoidal surface at its distal side that is wider in the radial-ulnar direction than in the volar-dorsal direction, wherein said first ellipsoidal surface is concave and has a distal edge defining a central recess in its volar side which forms a guide surface, and wherein said radial brace member includes an elongated portion projecting in a proximal direction and defining a radius abutment surface, said elongated portion defining a plurality of laterally-oriented holes which are threaded;
a cover releasably mounted on said radial brace member, wherein said cover and said radial brace member together form a substantially spherical cavity which receives and rotationally supports said ball on said radial brace member; and
an articular member defining a second ellipsoidal surface that is convex and is slidably received by the first ellipsoidal surface;
wherein said first ellipsoidal surface extends in the ulnar direction beyond the longitudinal axis of said rod; and
wherein said second ellipsoidal surface defines a recess aligned with and extending proximally to the central recess in said first ellipsoidal surface.

10. A prosthesis as recited in claim 9, and wherein said radial brace member further defines a proximal convex surface which lies opposite said first ellipsoidal surface and includes means for being received in a natural recess at the distal end of a human radius bone without changing the overall length of the radius bone.

11. A prosthesis as recited in claim 10, wherein said ulnar brace member is configured for mounting on the ulna bone of a patient,
said articular member includes means for mounting on at least one carpal bone of the patient;
and said ball and said spherical cavity provide the same axis of rotation and the same alignment of the radius and ulna as a natural radioulnar joint.

\* \* \* \* \*

UNITED STATES PATENT AND TRADEMARK OFFICE
CERTIFICATE OF CORRECTION

PATENT NO. : 8,333,806 B2
APPLICATION NO. : 12/098034
DATED : December 18, 2012
INVENTOR(S) : Luis Roman Scheker It is certified that error appears in the above-identified patent and that said Letters Patent is hereby corrected as shown below:

Column 3, line 51, delete "boric" and insert therefor --bone--.

Column 7, Claim 1, line 7, delete "in".

Signed and Sealed this
Twelfth Day of March, 2013

Teresa Stanek Rea
*Acting Director of the United States Patent and Trademark Office*